United States Patent
Melendez et al.

(10) Patent No.: US 6,692,697 B1
(45) Date of Patent: Feb. 17, 2004

(54) VERSATILE FLOW CELL FRONT-END FOR OPTICALLY-BASED INTEGRATED SENSORS

(75) Inventors: Jose L. Melendez, Mayaguez, PR (US); Jerome L. Elkind, Richardson, TX (US)

(73) Assignee: Texas Instruments Incorporated, Dallas, TX (US)

( * ) Notice: Subject to any disclaimer, the term of this patent is extended or adjusted under 35 U.S.C. 154(b) by 277 days.

(21) Appl. No.: 09/615,289

(22) Filed: Jul. 13, 2000

Related U.S. Application Data

(60) Provisional application No. 60/146,475, filed on Jul. 30, 1999.

(51) Int. Cl.[7] .................................................. B01L 3/00
(52) U.S. Cl. ........................ 422/57; 422/100; 422/103
(58) Field of Search ......................... 422/82.05, 82.08, 422/82.09, 99, 100, 103, 57

(56) References Cited

U.S. PATENT DOCUMENTS

| | | | |
|---|---|---|---|
| 5,313,264 A | | 5/1994 | Ivarsson et al. |
| 5,443,890 A | | 8/1995 | Ohman |
| 5,639,423 A | * | 6/1997 | Northrup et al. ............. 422/50 |
| 6,033,544 A | * | 3/2000 | Demers et al. .............. 204/450 |
| 6,146,103 A | * | 11/2000 | Lee et al. ....................... 417/50 |
| 6,184,029 B1 | * | 2/2001 | Wilding et al. ........... 435/287.1 |
| 6,326,612 B1 | * | 12/2001 | Elkind et al. ................ 250/239 |
| 6,358,387 B1 | * | 3/2002 | Kopf-Sill et al. ........... 204/603 |

FOREIGN PATENT DOCUMENTS

| | | |
|---|---|---|
| EP | 0 855 591 A2 | 7/1998 |
| WO | WO 98/05424 | 2/1998 |
| WO | WO 9933559 | * 7/1999 |

* cited by examiner

*Primary Examiner*—Jeffrey Snay
(74) *Attorney, Agent, or Firm*—J. Dennis Moore; W. James Brady, III; Frederick J. Telecky, Jr.

(57) ABSTRACT

A versatile flow cell front-end (104) for storing and delivering reagents, test samples, and other transportable materials within an optically-based integrated sensor device (100), where management of those materials is controlled via electrical connections (110, 114) within the optically-based integrated sensor device is disclosed, including an inlet chamber (118) formed within the flow cell, a sensing chamber (116) formed within the flow cell, an electrical interface (114) formed within the flow cell, a conduit (122) adjoining the inlet and sensing chambers, another conduit (124) adapted to dispose of fluid in the sensing chamber, and a fluidic control member (126) instantiated along the conduit and responsively coupled to the electrical interface.

10 Claims, 3 Drawing Sheets

VERSATILE FLOW CELL FRONT-END FOR OPTICALLY-BASED INTEGRATED SENSORS

This application claims priority under 35 U.S.C. § 119 (e)(1) of provisional application No. 60/146,475 filed Jul. 30, 1999.

FIELD OF THE INVENTION

This invention relates in general, to sensor systems in the fields of chemical, biochemical, biological, and biomedical analysis, and in particular to, to a versatile flow cell element for use in conjunction with an optically-based sensor.

BACKGROUND OF THE INVENTION

Optically-based sensors are utilized in connection with analytical measurements of a wide variety of analytes for sensor systems in the fields of chemical, biochemical, biological and biomedical analysis. Such sensors typically employ refractive index or surface refractive measurement. In many conventional sensing systems, analytical measurements are primarily conducted in a centralized testing environment. This generally requires that a sample of interest be brought to a specially equipped lab for analysis. Such a testing environment restricts measurements to those that can tolerate delays effected by, as well as costs imposed by, such a methodology. As often is the case with the use of biomedical sensors in medical emergencies, for example, analytical determinations must be immediately made in-situ.

When used in various biochemical applications, optically-based sensor systems typically utilize a variety of additives or reagents in processing a particular analyte. For example, a desired sample might be collected, then washed with a solution, mixed with a reagent, and finally rinsed before analysis. Conventional optically-based sensor systems thus require a variety of apparatus and hardware (e.g., flow cells, reagent vessels, pumps), which are usually modular and somewhat cumbersome in nature. Furthermore, construction and assembly of optically-based sensor system equipment typically requires provisions for management of not only electronic, but also fluidic, mechanical, and optical interfaces between the sensor device and the host end equipment. In conventional sensing methodologies, optical connections, fluidic connections and electrical connections to a host unit have usually been made in a series of steps. Typically, a sensor is first plugged into its electrical socket, and subsequently, an inlet tube is inserted into a flow cell. Optical connections are then achieved, and precise optical alignment and calibration are made. Such a methodology is time-consuming and difficult and does not generally allow for analytical measurements to be taken easily, rapidly and accurately at the point of need. Moreover, while electronic connections may be standardized in a wide variety of handheld and mobile end equipment, fluidic connections are widely non-standard and often complicated. These non-standard fluidic connections can cause system level problems associated with assurance of non-leaking connections and connection lifetime and reusability, as well as practical application limitations associated with increased end equipment complexity, size and costs.

In instances where a small sample is to be processed, or where only a limited number of sample processing steps are required, such conventional systems are generally inefficient in terms of cost and performance. A number of fluidic, mechanical, or electrical connections may be made to vessels or apparatus for reagents and materials not required for a particular analysis of interest. Previously, some attempts have been made to overcome some of these limitations through the use of microfluidics. Microfluidic chips have been produced using microfabrication techniques, providing small-scale sample routing and processing channels in an organic or manufactured medium. These chips, however, still require manual sample manipulation and management of electronic, mechanical, and optical interfaces. Usually, a sensing device has no direct electronic interaction with the chip—any data relayed to the sensing must be through optical means (e.g., spectral projection). Commonly, a desired sample must be manually inserted into the chip. In some such systems, other manual or mechanical interaction (e.g., puncturing a cell containing a reagent) is required for proper processing. And because of the reduced scale of such systems, precise optical alignment and calibration are often more critical, and harder to achieve, than in larger conventional systems.

SUMMARY OF THE INVENTION

Therefore, a versatile flow cell front-end for storing and delivering reagents, test samples, and other transportable materials to an optically-based integrated sensor device, where management of those materials is controlled via electrical connections within the optically-based integrated sensor device, is now needed; providing cost-effective and efficient performance while overcoming the aforementioned limitations of conventional methods.

The present invention provides an optically-based integrated sensing system having a versatile flow-cell front end element for storing and delivering reagents, test samples, and other transportable materials to an optically-based sensor device, wherein management of those materials is controlled via electrical connection within the optically-based integrated sensing system, and wherein the flow-cell front end element is adapted to engage with, or is formed together with, that optically-based sensor device, forming a cohesive and self-contained sensing unit.

More specifically, the present invention provides an integrated flow cell having an inlet chamber, a sensing chamber, and an electrical interface all formed within the flow cell, a first conduit adjoining the inlet and sensing chambers, a second conduit for disposal of fluid from the sensing chamber, and a fluidic control member instantiated along the first conduit and responsively coupled to the electrical interface.

The present invention further provides an optically-based integrated sensor comprising a sensor device having a sensing element and an electrical interface, and a fluidic processing element removably engaged with the sensor device, and having a fluidic handling system and a fluidic control system, coupled and responsive to the electrical interface, formed within.

The present invention also provides a method of producing a disposable optically-based integrated chemical or biochemical sensor, by providing a sensor device having a sensing element and an electrical interface, providing a fluidic processing element, having a fluidic handling system and a fluidic control system, coupled and responsive to the electrical interface, formed within and adapted to securably engage with the sensor device, and engaging the sensor device and the fluidic processing element.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

Figure 1:
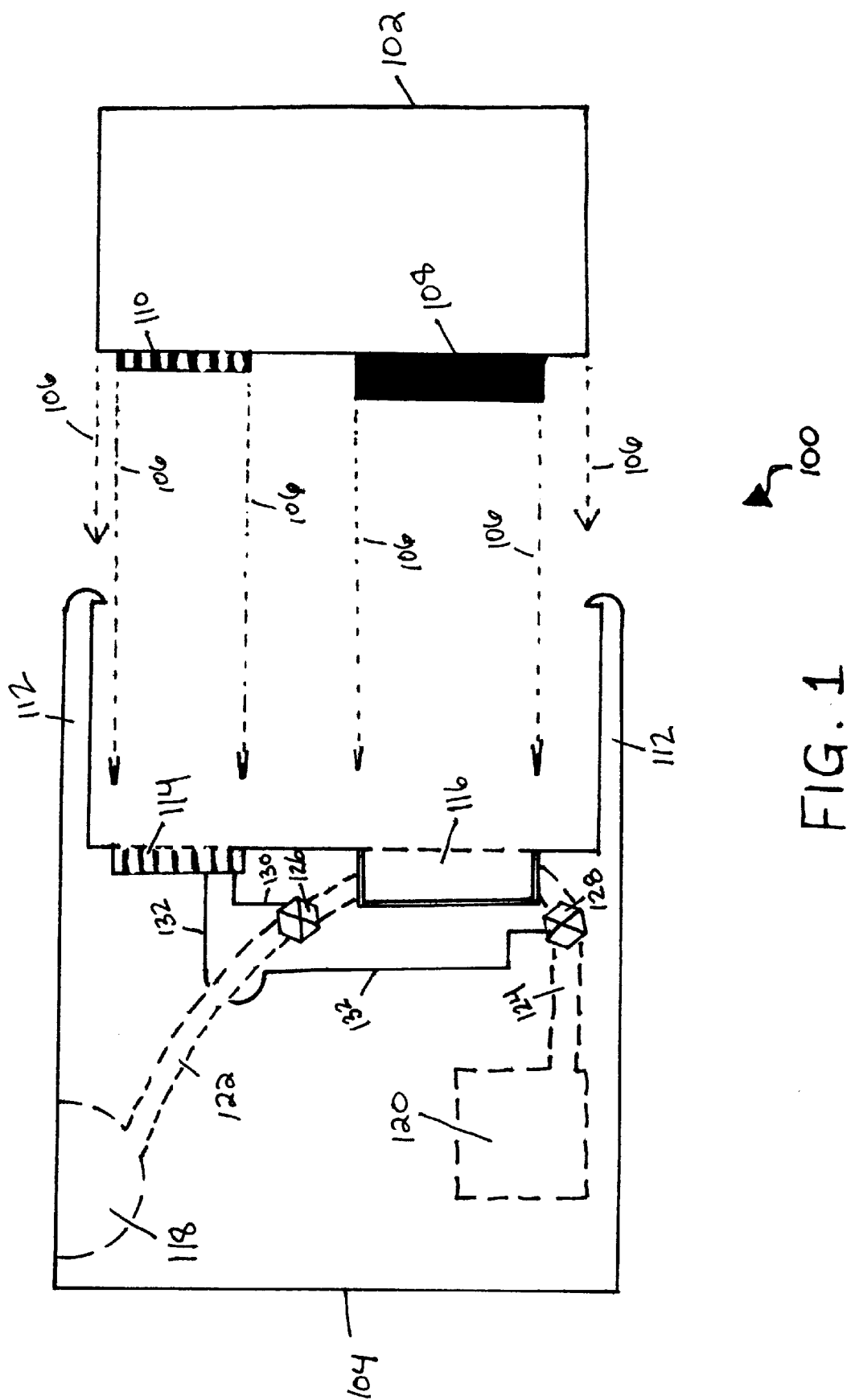
FIG. 1 is an illustrative diagram of one embodiment of a flow-cell front end element according to the present invention.

While the making and the use of the present invention is discussed in detail below, it should be appreciated that the present invention provides many applicable inventive concepts which can be embodied in a wide variety of specific contexts. The specific embodiments discussed herein are merely illustrative of specific ways to make and use the invention, do not delimit the scope of the invention.

The present invention provides storage and delivery of reagents, test samples, and other transportable materials within a hybrid flow cell attachment to an optically-based chemical or biochemical sensor device. Management of these materials is provided through electrical connections with the optically-based sensor device, which may in turn be interfaced physically or wirelessly to a particular end equipment. The present invention provides integrated fluidic processing functionality in an efficient manner, such that high performance disposable sensor systems may be produced if desired. The present invention comprehends, and is equally applicable with, the use of a variety of optically-based sensor devices. Some examples of such devices include surface plasmon, critical angle, and fluorescence based sensors.

Summarized briefly, a surface plasmon is a surface charge density wave at the surface of a dielectric interface having a thin conductive film formed thereon. The oscillation of free electrons at a conductor-dielectric boundary is affected by the refractive index of the material adjacent to the film. Using a polarized beam of monochromatic light, surface plasmon polaritons can be excited. Resonance occurs when the polarized light is totally internally reflected from the conductive film. The light internally reflected from the film has a minimum intensity at the resonance angle. By detecting the resonance angle, the refractive index of a material adjacent to the film may be determined, which is indicative of other properties of the material.

Critical angle measurement sensors rely on the principle that critical angle is a mathematical function of refractive index, and thus, determination of the critical angle gives rise to the determination of the refractive index of a sample, which is indicative of one or more sample properties, from which further qualitative and quantitative analyses about the sample may be made. In a critical angle sensor, when polarized light rays are directed to a sample of interest at angles of incidence smaller than the critical angle, a portion of the light is refracted into the sample, resulting in an overall loss. At angles of incidence larger than the critical angle, total internal reflection occurs, and the full intensity of the light is reflected off the sample. The critical angle, and consequently the refractive index, may be then determined by measuring the intensities of the reflected light rays, and detecting a transition from a high intensity to a low intensity.

The use of fluorescence based methodologies to detect sample gases and liquids typically involves the molecular labeling of a film or other article followed by excitation and fluorescent measurement in the presence of the particular sample of interest. Fluorescent labeling involves the deposit of a suitable fluorescence chemistry known to interact with the sample of interest. A source of excitation light is directed at the coated article, which when brought in contact with the sample, emits a low intensity fluorescence energy. A photodetector may be used to measure the emission and therefore detect the presence of the sample.

Although equally applicable with these and other similar sensor devices, the present invention is hereinafter described in relation to a surface plasmon type sensing device, for purposes of illustration and explanation.

Among other things, the present invention recognizes that certain applications require greater flexibility and efficiency than the often cumbersome, non-portable conventional chemical and biochemical sensor systems. The present invention overcomes these and other conventional limitations by efficiently consolidating all necessary handling and processing of analytical materials into a single, integrated flow-cell front end. The present invention couples a flow-cell front end element with an appropriate optically-based sensor device to produce an optically-based, integrated chemical or biochemical sensor unit. The present invention eliminates the need for end equipment to interface with optically-based integrated sensor units by non-electronic means. The present invention further eliminates the need to provide fluidic connections to a host reader or end-equipment, rendering preparation of the optically-based, integrated chemical or biochemical sensor units independent of any fluidics constraints. All necessary fluidics are provided for through the integrated flow-cell front end element.

The present invention is now described in greater detail with reference to FIG. 1. FIG. 1 depicts one embodiment of an optically-based integrated sensor assembly 100 according to the present invention. Assembly 100 may be constructed by coupling together a sensor device 102 and an integrated flow-cell front end element 104 as indicated by arrows 106. Sensor 102 comprises a sensing apparatus 108 and an electrical interface 110. As depicted, apparatus 108 can be a sensing surface of the type associated with surface plasmon sensors. Apparatus 108 may also comprise any other suitable contrivance for sensor or reader interaction with the desired analyte, depending on a user's particular design considerations. As depicted, interface 110 is a male-type connector and may comprise a card-edge type electrical connector, an array of pin-type connections, or any other suitable contrivance for establishing electrical connection. Alternatively, interface 110 may comprise a female-type receptacle or socket formed to receive an electrical connector.

Front-end 104 may comprise coupling structure(s) 112, electrical interface 114, and sensing chamber 116. Element 104 further comprises inlet chamber 118 and receptacle 120. Inlet 118 is fluidically adjoined to chamber 116 by conduit 122, and receptacle 120 is fluidically adjoined to chamber 116 by conduit 124. Fluidic control members 126 and 128 are instantiated along conduits 122 and 124, respectively. Members 126 and. 128 are coupled to interface 114 by leads 130 and 132, respectively.

Coupling structure(s) 112 may comprise a member or plurality of members formed as part of, or disposed upon, front-end 104 that are adapted to engage sensor 102 securely; providing efficient coupling of apparatus 108 with chamber 116, and interface 110 with interface 114. Structure 112 may provide a clip-on or snap-on engagement with sensor 102 as depicted. Alternatively, structure 112 may be adapted to provide clamp on, screw on, or friction engagement with sensor 102. Other arrangements or contrivances are contemplated, as long as the necessary inter-coupling of sensor 102 and front end 104 is achieved. Optionally, one or more gasket members (not shown) may be formed or disposed upon member 104 or structure 112 to provide a secure seal (e.g., leak-proof).

Interface 114 is formed within element 104 and adapted to communicatively engage with interface 110. As depicted, interface 110 is a female-type connector and may comprise a card-edge type electrical receptacle, an array of pin-type sockets, or any other suitable contrivance for establishing electrical connection. Alternatively, interface 110 may comprise a male-type connector or array of pins formed to establish electrical connection.

Chamber 116 is formed as a cavity within element 104 to receive and house sensing apparatus 108, and to provide fluidic access to apparatus 108 from conduits 122 and 124. Alternatively, chamber 116 may be formed as part of either conduit 122 or 124, adapted to receive and house apparatus 108. Efficient alignment of apparatus 108 within chamber 116 may be pre-determined and provided through the structure of chamber 116 (e.g., particular shape or angulation), or through structure 112, or both. Inlet chamber 118 is formed as a cavity within member 104 to receive or collect a desired analyte. The shape and size of chamber 118 may be varied depending on particular analytical requirements. Inlet 118 may comprise an open cavity within front end 104, requiring only immersion or submersion in a desire analyte for collection. Alternatively, inlet 118 may include a restrictive covering (e.g., a shutter device or a membrane) over its opening in a surface of front end 104, requiring manual insertion (e.g., opening a shutter or piercing a membrane) of a desired analyte. Conduit 122 comprises a channel or trench formed within element 104 fluidically coupling a bottom portion of inlet 118 to an upper portion of chamber 116. Fluidic control member 126 is instantiated Along conduit 122, somewhere between inlet 118 and chamber 116. Member 126 may comprise any suitable valve, pumping mechanism, or flow control contrivance that is electronically controllable to manage the flow of fluids in conduit 122. Member 126 may move or restrict fluidic movement in conduit 122 by means of electric or electromagnetic fields, temperature variation, or electro-mechanical features. Member 126 is communicatively coupled to interface 114 by lead 130.

Receptacle 120, conduit 124, fluidic control member 128, and lead 132 are substantially similar in structure and formation to inlet 118, conduit 122, member 126, and lead 130 respectively. Receptacle 120 is formed within member 104 to receive or dispose of analyte from chamber 116. The shape and size of receptacle 120 may be varied to control the amount of analyte that front end 104 will process, depending on particular analytical requirements. In one alternative embodiment, receptacle 120 may be formed proximal to a surface of element 104, including a restrictive covering (e.g., a shutter device or a membrane) over its opening in the surface of element 104, to allow for processing adjustments or repeated use of element 104. Another alternative embodiment may eliminate the presence of receptacle 120 altogether, forming conduit 124 from chamber 116 directly to a surface of front end 104, with or without fluidic control element 128, for disposal of analyte from chamber 116.

Operationally, assembly 100 may function as follows. Sensor 102 and front end element 104 are coupled together; engaging interfaces 110 and 114 with each other, and engaging apparatus 108 within chamber 116. Sensor 102 may be communicatively linked to a particular end equipment by either an actual physical connection (e.g., electronic interface or cable), or by a remote connection (e.g., infrared or wireless communication). Once combined, assembly 100 forms a versatile optically-based integrated sensor capable of numerous fixed and remote applications and uses. A desired analyte may be manually introduced into inlet 118 or, alternatively, assembly 100 may be immersed or submerged in a desired analyte (e.g., dropped into a stream or vat) causing inlet 118 to fill. Sensor 102 provides electrical control signals via interfaces 110 and 114, and lead 130, to fluidic control member 126. Responsive to this control, member 126 operates to allow or facilitate movement of the desired analyte through conduit 122 towards chamber 116. Upon reaching chamber 116, the analyte may be allowed to flow around or across apparatus 108, while it performs its intended analysis. Utilizing electrical control signals provided by sensor 102 via interfaces 110 and 114, and lead 132, fluidic control member 128 may allow or facilitate movement of the analyte out of chamber 116 into receptacle 120 via conduit 124. Depending on the nature of the testing or the materials used in its fabrication, assembly 100 might be re-used or simply disposed of after analysis completion. The fluidic handling system functionality of chambers 118, 116, and 120, and conduits 122 and 124, in combination with fluidic control system functionality of elements 126 and 128, and their responsive coupling to interface 114, provide a versatile and integrated fluidic processing system within the flow cell element 104; replacing numerous modular and cumbersome equipment and connections associated with conventional fluidic analysis and processing.

Front end element 104 may be formed or produced by any suitable methods or processes, such as semiconductor processing, injection molding or plastic encapsulation, that consolidate all the requisite and desired functionalities into a single, efficient, integrated flow cell element. Fluidic connections with host and sensoring end equipment is eliminated, as all processing occurs in front end element 104, using only electronic control. Versatile and robust analytical tools can thus be produced in an inexpensive and disposable format.

Figure 2:
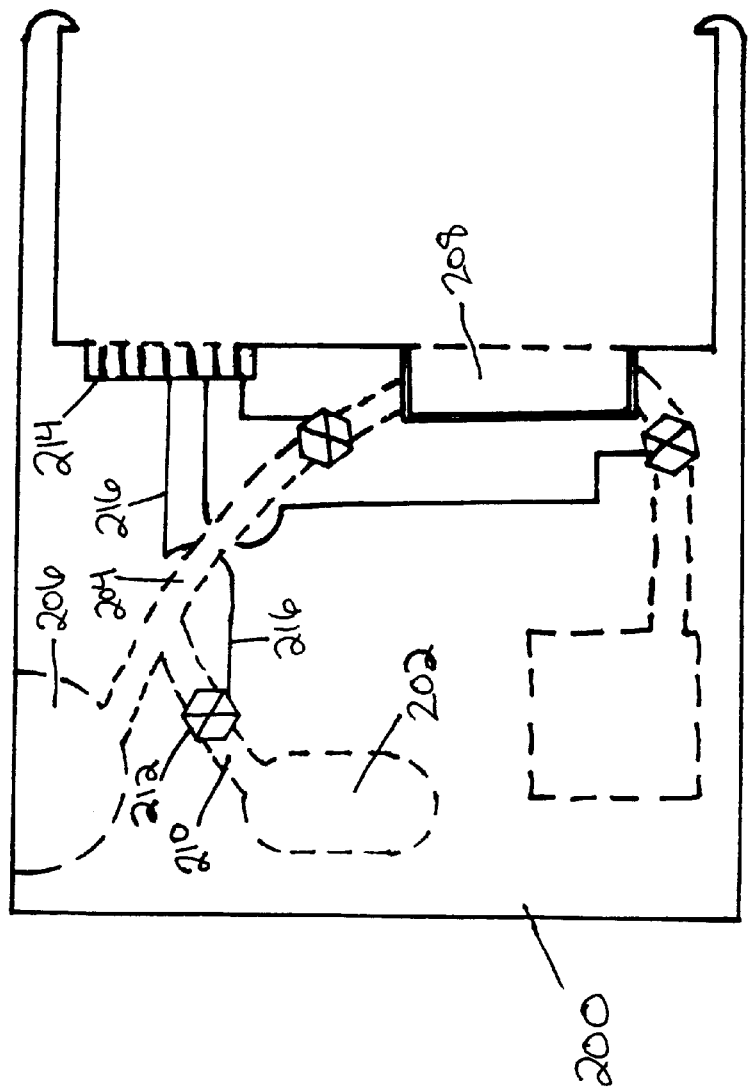
FIG. 2 is an illustrative diagram of another embodiment of a flow-cell front end element according to the present invention.

Referring now to FIG. 2, another embodiment of the present invention is illustrated. FIG. 2 depicts another flow-cell front end element 200 according to the present invention. The structure and formation of element 200 is similar to that of element 104 as depicted in FIG. 1, and would also be engaged with a sensor 102 to provide an integrated optically-based sensor assembly according to the present invention. Element 200 further comprises one or more reagent chambers 202 formed within element 200. Each chamber 202 is coupled to the main conduit 204, connecting inlet chamber 206 and sensing chamber 208, by a conduit 210. Alternatively, conduit 210 may couple a reagent chamber 202 directly to sensing chamber 208. A fluidic control member 212 is instantiated along conduit 210 between chamber 202 and conduit 204, and is communicatively coupled to interface 214 by a lead 216. A chamber 202 may be pre-loaded with a particular agent or compound to be later introduced, via member 212, to an analyte of interest passing through conduit 204. Alternatively, a chamber 202 may be employed within element 200 to collect or store a particular sample of an analyte, providing for sequential or time-based analysis. Optionally, additional fluidic control elements might be instantiated along the conduits to facilitate or control the mixing or interaction of an analyte and the reagent from each chamber 202.

Figure 3:
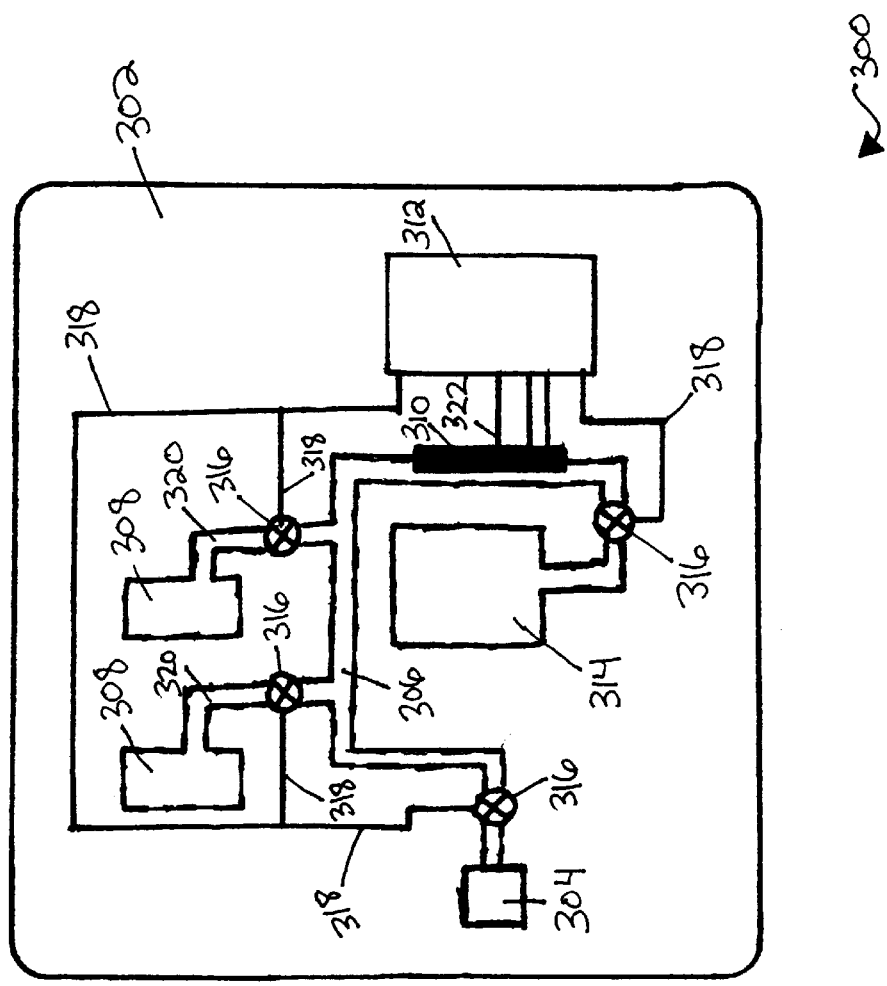
FIG. 3 is an illustrative embodiment of a fully integrated, optically-based analytical assembly according to the present invention.

FIG. 3 illustrates an optically-based integrated sensor 300, according to the present invention, produced in as a single, efficient, semiconductor type of product. Sensor 300 comprises a single substrate 302. Upon or within substrate 302 is formed or disposed: an inlet chamber 304, a primary channel 306, one or more reagent chambers 308, a sensing element 310, a sensing control device 312, a receptacle chamber 314, multiple fluidic control members 316, electrical leads 318, and reagent channels 320. A desired analyte is applied via inlet 304. Responsive to signals generated by control device 312, fluidic control members 316 are employed to allow or facilitate flow of the analyte along channel 306. Control device 312 may be a more sophisticated control device, such as a microcontroller or microprocessor, or may merely be a simple communications relay device, transferring control signals received from an end equipment external to sensor 300.

As depicted in FIG. 3, sensing element 310 is communicatively coupled to control device 312 by one or more leads 322, and is at least partially instantiated within channel 306. Alternatively, an additional chamber could be formed within sensor 300 to provide element 310 access to the analyte, depending upon particular design constraints or needs. Elements 316 are further controlled to allow or facilitate the flow of the analyte past sensing element 310 and into receptacle 314. Reagents from chambers 308 may be mixed with or introduced to the analyte in channel 306 by control elements 316, via reagent channels 320. Alternatively, chambers 308, channels 320, and their associated control elements 316 and leads 318 may be eliminated from sensor 300 for a simpler processing requirement. In sensor 300, the constituent elements may be formed utilizing available semiconductor production processes and methods (e.g., etching, deposition), or other suitable materials and processes depending on particular analytical needs and intended uses.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. The teachings and concepts of the present invention may be applied to a variety of sensor devices and applications. The principles of the present invention are practicable in a number of technologies. It is therefore intended that the appended claims encompass any such modifications or embodiments.

What is claimed is:

1. An integrated flow cell for sensing a Parameter of a fluid sample, comprising:
   an inlet chamber formed within the flow cell;
   a sensing chamber formed within the flow cell;
   an electrical interface formed within the flow cell;
   a first conduit adjoining the inlet and sensing chambers;
   a second conduit adapted to dispose of a fluid in the sensing chamber; and
   a fluidic control member disposed along the first conduit, adapted to control the flow of the sample from the inlet chamber to the sensing chamber, and responsively coupled to the electrical interface.

2. The flow cell of claim 1 further comprising an engagement structure disposed upon the flow cell and adapted to secure the flow cell to a sensor device.

3. The flow cell of claim 1 further comprising a second fluidic control member disposed along the second conduit and responsively coupled to the electrical interface.

4. The flow cell of claim 3 wherein the flow cell further comprises a receptacle chamber formed within the flow cell and the second conduit adjoins the sensing and receptacle chambers.

5. The flow cell of claim 1 wherein the inlet chamber further comprises a restrictive covering disposed along a surface of the flow cell.

6. The flow cell of claim 2 wherein the flow cell further comprises a gasket member disposed along a surface of the flow cell.

7. The flow cell of claim 4 wherein the sensing chamber is formed as a contiguous portion of the first conduit.

8. The flow cell of claim 4 wherein the sensing chamber is formed as a contiguous portion of the second conduit.

9. The flow cell of claim 4 further comprising:
   a reagent chamber formed within the flow cell;
   a third conduit adjoining the reagent chamber and the first conduit; and
   a third fluidic control member disposed along the third conduit and responsively coupled to the electrical interface.

10. The flow cell of claim 4 further comprising:
    a reagent chamber formed within the flow cell;
    a third conduit adjoining the reagent chamber and the sensing chamber; and
    a third fluidic control member disposed along the third conduit and responsively coupled to the electrical interface.

* * * * *